(12) United States Patent
Kapulnik et al.

(10) Patent No.: US 6,844,484 B2
(45) Date of Patent: Jan. 18, 2005

(54) ARABIDOPSIS BIO2 GENE PROMOTER

(75) Inventors: Yoram Kapulnik, Karmei-Joseph (IL); Anat Kahana, Rosh Ha'ain (IL); Ayelet Bar-Akiva, Gizo (IL); Rozalina Ben-D V, Tel Aviv (IL); Smadar Wininger, Rishon LeZion (IL); Idit Ginzberg, Raanana (IL)

(73) Assignee: The State of Israel - Ministry of Agriculture & Rural Development, Beit-Dagan (IL)

( * ) Notice: Subject to any disclaimer, the term of this patent is extended or adjusted under 35 U.S.C. 154(b) by 118 days.

(21) Appl. No.: 09/983,183

(22) Filed: Oct. 23, 2001

(65) Prior Publication Data

US 2003/0101475 A1 May 29, 2003

Related U.S. Application Data (60) Provisional application No. 60/308,581, filed on Jul. 31, 2001.

(51) Int. Cl.[7] .................. C12N 15/82; C12N 15/90; C12N 15/64; A01H 5/00

(52) U.S. Cl. ................. 800/278; 435/320.1; 435/419; 536/24.1; 800/286

(58) Field of Search .................. 435/69.1, 320.1, 435/419, 468; 800/278, 286, 288, 295, 298; 536/23.6, 24.1

(56) References Cited

U.S. PATENT DOCUMENTS 5,869,719 A * 2/1999 Patton ..................... 800/278

OTHER PUBLICATIONS

Weaver et al., Plant Physiol., 1996, vol. 110, pp. 1021–1028.*
Weaver et al., GenBank Accession No. U24147.*
Van der Krol et al., Nature, 1988, vol. 333, pp. 866–869.*

* cited by examiner

Primary Examiner—Ashwin Mehta
(74) Attorney, Agent, or Firm—G.E. Ehrlich (1995) Ltd.

(57) ABSTRACT

A recombinant promoter which is functional in plant cells, the recombinant promoter comprises SEQ ID NO: 9.

18 Claims, 7 Drawing Sheets

(7 of 7 Drawing Sheet(s) Filed in Color)

LhbIB2 PROMOTER
aagcaagtcc tctgcttctc ccattggacc
atctccggcg actctgtagc cctcaacagc tcccatgagg ataacttgag tagcccaaat
ggctaagatg ctctgagcgt ggaccaagct cgggttgccc aagtagtcca atcctccgtc
gctgaagatc tgtgaaccag ccttgaacca aaccgcttct ccgaacttca ctccgttcct
agccaatagc tcagggaaaa cgcagcctag ggctccgagc atgcccatc tgctgtggat
aacttctagc tcacggttcc tagcgaaggt ctcgggatcg gcggatagac cggcagtgtc
ccacccgtaa tcaccggga actctccagt gaggtagctc ggaggctcac cggagaatgg
acccaagtac ttgactcggt cggatccgta ccatgggctg ccggatggac cggtgggctt
ggaggctttg cgcatggtga ttcggccggt tccaaatact tcggaggccg ccggggatag
cttaacggcc tttccggtca aagcaggaga ggagagagcc attgtcgagg cggccattgc
ggtgagagtg tggcgcaagt aaaaggctct ttagttaata agatgtgatg aaattggata
gctaggttac ggtgaggttt ttgggtattt ataacgtaca tatgaattgc aaaacttgaa
gatttaattt gcttatctcg tgatatcgtc aatgccttga tttctattgg ttgttgacat
ttttgagctt agattttttg tcttgtcgag ctggcatcag attttggtt tggaattgag
ttgtgttaga taaattagat atctcgtagc atcttagcat attggaatac ccattgtcca
ttgaagacgt gccacttgta aatctgacgt gtttctatcc ctttgaatcg tatcagtctc
aaggtacacg tcattggtgt ttcccaaata gacatgtcgt caaagaatca aaacaacatg
atacaaagtc caaacatact tagaacgttg catactaccc actctttcac caaaatgtga
aatatgagtg aaaactgaac atctcaattt tcattactct aagtttgtta attatcttgt
taaaaaact actctaaatt acagaagatt taatcctgat aagaaagtac attaaaatga
caacaaagta aaaaaaaaaa atacagttca tcttcaaaga catgttttct aattcgtatt
ggcaagaaaa acttaccagt catatttgtt gccgaaaaca ttcaacaaaa tcaatcaaag
gtatcagtta atatcattgt cgacggtttt atattattaa cttatgatcg taagaacttc
gtatcactt ttgtttcatc taactgcatt gttttacata acattgatat atattgttt
ggtaagtgtt tctagtttca cttaaaaact ttgtagtttg gcgttcgaaa caacttgat
aagagaaaaa agaaaatatt attgagagca tgaagtggat tgaattaaa gaaaacaagg
aaaaagaaaa aaatagattg gaataatttc aaatatttct ttccaataat tcaagcattt
atctttgaaa atttcccaa agtttctttg tgtacaaatg acaagtgttt tcgttgcagc
taaagaatct agaaaagct tatggactag agagtgacac ataggacaag ataacgacaa
tccaaaatc tataagcca atcactaaac agatacagat acttcacaga taacaaacct
tactcttaag attgctataa agtggacgta tacccaaacc attttcaatc actctcacca
gtcacaacca aaaaaagaa aacacaaaa caaagattat aATG

Fig. 3a ats3B PROMOTER

```
aaatgactta taaaagacag aaactagtca cttagatgga tgacttaaga cttaagagtt
aagactatct cactttcgaa aaatgattta tttagctgag gtgcggagtg gagtggacct
tgtgatcctt ttccctacac gaaagttttt tcgtgaccag ttaatgtgta ctttgtacac
gtttcttctc atatatatga ttgaaaaggg ggcatttgtg agcctgaagg tagtagtcgt
gatccatgag tgcatgacca tagttttatg tgactttaag atgagttctt gactccgttc
tacacctttg attacatact caagtttgca tggtggaaat cagcttgagg tgccatattt
gtgcttgagg gggccgtaag tgcaatggca tggtactcca aggagaacgg ttgcgtatgt
gggttcccca ttgttattgt gatgtgatca gagtcgcaag ataatcgtga gctgatatta
cttgttgatc tagaggcagc gtgcattacc tcatatagaa gataccatgg actttgggag
gttttttttgg aaattcttcc atgaggggtt taccgcgcac ttgatacatg tagatgatgg
ttttgccgtt tcgtttgttc gctcggtctc tttgtcccac aaacatatct tgcatgatgt
agttgttgtt agtatcgact caaatattta ctctctccaa ccagtaaggt tttgctttta
tcctagccac ataaaaatca gaaataaaag tactatttgc taaaaatgaa gtgaaagtat
tgaattaacc gaaatcaatg tattcaaatt ttgtctcgct tttcttttgt cgactaatat
attatcattt gaagataata tataactttt ccaacaaaaa gattatcgac aatttattgt
ggtaaatgat tttcaggatg tatccagaat cgacagtcta ccagtactag aatatatcta
atagataaat ggttcttctt acactatgct cattatggat tctttaattt actctttcac
aaaagggacg atgacgaagg agtctctcta cagcacgtta gaattctttt gataggttta
cttccattag tctgaaatgg aatcttattt ataagtctgc ctgaaaaatc ttaacaattg
atattaataa aacggaaaga gtgatgaata ttttttaagag catctcgaat ctatctctat
ttttatttat atactctatt tttgtattta tttaactcta actcatctct attttcattt
gtaaaataga aatttctaat ttttttttaa agcaaaaaat agagattttt atttttctc
ttatttattt tttctaacga attttgagg aaccattaaa gttaaaatat aaatctctat
tatatttttt cctctatatt cagaaagaaa ataatagaaa caaacattgg agatggttaa
agcttttttt tttgtccgga taaatatcat acaatatatt tatgtaaata tcaaatttaa
ataattttct tataactatt ttttaatgcg accttatttc caaagaaagt gttaagccaa
attaaatcat acatggtaaa taagaggtcc aaaagaccaa aagcattaaa tttaaggtaa
tgcgtctgat ttcttttctc ccaaacgaaa ggagccaaaa gcaaccgatc aagtggagac
cagtaaccgc acattcactt catttccccc acaagagaaa agataagata atggagtttt
ctgccacgtg gccttatcct agtggtgcgt accgataagg tgtcaacac ctttccttaa
tcctgtggca gtaaacgacg ttatcatgaa tcatggaccc tttgatcatg agggcttttc
gcctttaggg ggttctcatt atataaagat gacaaccca gtaggaaaac aagtcagtaa
gtaaacgagc aaaagaagaa gagaaacaac aagaagtagt aATG
```

Fig. 3b

AtBio2 PROMOTER

```
aactcttttc ccgataatat tcttcctctc catccgacac gcttccittt ctccttggag gtgatgggat
ctgcatccaa caagtaagtt gtggtaccaa gatttagtt tacaaactat cagctttcca ctagacacat
tgaacaaccc atttaatata ttatttctag cagaagaaca ttaacaaatg cccaataag atagcaccag
agacagaaca ggggtaaagt tcaaatgact atagagtggt ggtgaagttc aagacatggt agacctgtgt
gcgcgacata tatcttcct caggcggaag ctgaataccg agcttttca aatcttcatg agggattggt
cgtctgatat taacaaatag aaagaatgcc catttcatga ccactatgtt tagctggtgt tatctctgga
catgctaaag gaagagtaaa gcaaaaccat acaagggagc acggaatggt ctatctcgtc ctccaaagcg
aagttgtccg gatttcttcc taccaccaag gccacctcct gttaagagag aaatagattt catctgtaag
ggatgaaaat ataacgccta tgacatttca ttacagacaa aaataaaggt aaagaatggc aaacctagtc
ttcttggtat ccatccaggc atcaattgct gtctattata atcaacaata atctctcgcc catctattag
tgaatgatga gcatcctgct aaagaaacac caaaaaatt ctcactctga taaacaaact ccactagttt
ccagtaatta cacggagatg ttaatgaaac aatcacattg cggtgcctta gtaagtggtt cagacagctt
tcaacaacaa aaacaagagg taaaagaaa atgcaattta gtatcacagc acctcataag cacgaagcat
ctcctttca gtctcatact ccacaaaacc atatcctcgt gaagctccg tcactaaaaa aaggtaacaa
gaagaggaga ctcaatacta cacaatgtgg aacttagagg aaatatgtaa tcacagttct gcttagacaa
atatcttggt agaaagtaac aaacatcag aaatagaaag atgataaatt tcctaaagat aaagcaaagt
gttgatgtca taagtagagc aattgcaaaa tcttaccaat gtgtcttacc aagcgcaagt tcttaatcct
gccatactta ctcatcactt acgaagaaga aactttata atcatattca aaacatagtc tacacgaaaa
tcaaaaacta agtgaaattt ccatcattaa cctctcgaag tgtatcctcc gtagtgtgat gagagagacg
acccacgaag agagtacagt aaggatctcc aacagcctc gaatcaccag aaggatcatc tttcaaaaca
acccaaatca atgtatttga attcagaaac caaacgataa aagtgaaaag aggagcagag agaacgagag
agtatacata cataagccag cgttataaca gagaagagct cgacggacgc cgttatcatg tggagcaaca
tcagttccgt cgatacttcc ggcttgaatc ggatgatacg acgtcgcgta gaacactttg ttcacgacgt
tgtttcctcc gccgtcatt tcttctcccc cgactctctc tctctcacgg cggctccggc tgtttaagga
aataaagaat aacgtcgtcg tttgaattga ttactattaa aaagcccaac atataaattg ggcttattac
agcccagttta aagatatatg atattctcgt aggtcccaca ctaaggcgga aactccaacg gtggctgctt
tgggttagut gaatcactca ctgaagagtg aaaagctcta gcacaaacca aacaccaaat ctcattctct
cttcttcttc ttttccaca ttttctgatt agcagatcaa ATG
```

Fig. 3c

SEQUENCE LISTING

<160> NUMBER OF SEQ ID NOS: 9

<210> SEQ ID NO 1
<211> LENGTH: 31
<212> TYPE: DNA
<213> ORGANISM: Artificial sequence
<220> FEATURE:
<223> OTHER INFORMATION: synthetic oligonucleotide

<400> SEQUENCE: 1
gtaaggcctt cctctctacc gacacacttc c                          31

<210> SEQ ID NO 2
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 2
gtatctagag atctgctaat cagaaaatgt gg                         32

<210> SEQ ID NO 3

```
<211> LENGTH: 31
<212> TYPE: DNA
<213> ORGANISM: Artificial sequence
<220> FEATURE:
<223> OTHER INFORMATION: synthetic oligonucleotide

<400> SEQUENCE: 3
gtaaggcctc tagtaactta gatggatggg t                              31

<210> SEQ ID NO 4
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 4
gtaaggcctc tgacttgttt tcctactggt gttgtcatc                      39

<210> SEQ ID NO 5
<211> LENGTH: 31
<212> TYPE: DNA
<213> ORGANISM: Artificial sequence
<220> FEATURE:
<223> OTHER INFORMATION: synthetic oligonucleotide

<400> SEQUENCE: 5
gtaaggccta agtcctctgc ttctcccaat g                              31

<210> SEQ ID NO 6
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 6
gtatctagac gtccacttta tagcaatg                                  28

<210> SEQ ID NO 7
<211> LENGTH: 1874
<212> TYPE: DNA
<213> ORGANISM: Arabidopsis thaliana

<400> SEQUENCE: 7
aagcaagtcc tctgcttctc ccaatggacc atctccggcg actctgtagc cctcaacagc    60
tcccatgagg ataacttgag tagcccaaat ggctaagatg ctctgagcgt ggaccaagct   120
cgggttgccc aagtagtcca atcctccgtc gctgaagatc tgtgaaccag ccttgaacca   180
aaccgcttct ccgaacttca ctccgttcct agcaatagc tcaggaaaa cgcagcctag    240 ggctccgagc atggcccatc tgctgtggat aacttctagc tcacggttcc tagcgaaggt   300
ctcgggatcg gcggatagac cggcagtgtc ccacccgtaa tcaccgggga actctccagt   360
gaggtagctc ggaggctcac cggagaatgg acccaagtac ttgactcggt cggatccgta   420
ccatgggctg ccggatggac cggtgggctt ggaggctttg cgcatggtga ttcggccggt   480
tccaaatact tcggaggccg ccggggatag cttaacggcc tttccggtca agcaggaga    540 ggagagagcc attgtcgagg cggccattgc ggtgagagtg tggcgcaagt aaaaggctct   600
ttagttaata agatgtgatg aaattggata gctaggttac ggtgaggttt tgggtatttt   660
ataacgtaca tatgaattgc aaaacttgaa gatttaattt gcttatctcg tgatatcgtc   720
aatgccttga tttctattgg ttgttgacat ttttgagctt agatttttg tcttgtcgag    780
```

```
ctggcatcag attttggtt tggaattgag ttgtgttaga taaattagat atctcgtagc       840
atcttagcat attggaatac ccattgtcca ttgaagacgt gccacttgta aatctgacgt       900
gtttctatcc ctttgaatcg tatcagtctc aaggtacacg tcattggtgt ttcccaaata       960
gacatgtcgt caaagaatca aaacaacatg atacaaagtc caaacatact tagaacgttg      1020
catactaccc actctttcac caaaatgtga aatatgagtg aaaactgaac atctcaattt      1080
tcattactct aagtttgtta attatcttgt taaaaaaact actctaaatt acagaagatt      1140
taatcctgat aagaaagtac attaaaatga caacaaagta aaaaaaaaaa atacagttca      1200
tcttcaaaga catgttttct aattcgtatt ggcaagaaaa acttaccagt catatttgtt      1260
gccgaaaaca ttcaacaaaa tcaatcaaag gtatcagtta atatcattgt cgacggtttt      1320
atattattaa cttatgatcg taagaacttc gtatcacttt ttgtttcatc taactgcatt      1380
gttttacata acattgatat atatttgttt ggtaagtgtt tctagtttca cttaaaaact      1440
ttgtagtttg gcgttcgaaa caaacttgat aagaaaaaaa agaaaatatt attgagagca      1500
tgaagtggat tggaattaaa gaaaacaagg aaaaagaaaa aatagattg gaataatttc       1560
aaatatttct ttccaataat tcaagcattt atctttgaaa atttccccaa agtttctttg      1620
tgtacaaatg acaagtgttt tcgttgcagc taaagaatct agcaaaagct tatgggactag    1680
agagtgacac ataggacaag ataacgacaa tcccaaaatc tcataagcca atcactaaac      1740
agatacagat acttcacaga taacaaacct tactcttaac attgctataa agtggacgta      1800
taccccaacc attttcaatc actctcacca gtcacaacca aaaaaagaa aacacaaaaa       1860
caaagattat aatg                                                       1874

<210> SEQ ID NO 8
<211> LENGTH: 1964
<212> TYPE: DNA
<213> ORGANISM: Arabidopsis thaliana

<400> SEQUENCE: 8
aaatgactta taaagacag aaactagtaa cttagatgga tgggttaaga cttaagagtt        60
aagactatct cactttcgaa aaatgattta tttagctgag gtgcggagtg gagtggacct       120
tgtgatcctt ttccctacac gaaagttttt tcgtgaccag ttaatgtgta ctttgtacac       180
gtttcttctc atatatatga ttgaaaaggg ggcatttgtg agcctgaagg tagtagtcgt       240
gatccatgag tgcatgacca tagttttat tgactttaag atgagttctt gactccgttc        300
tacacctttg attacatact caagtttgca tggtggaaat cagcttgagg tgccatattt       360
gtgcttgagg gggccgtaag tgcaatggca tggtactcca aggagaacgg ttgcgtatgt       420
ggttcccca ttgttattgt gatgtgatca gagtcgcaag ataatcgtga gctgatatta        480
cttgttgatc tagaggcagc gtgcattacc tcatatagaa gataccatgg acttggggag       540
gttttttgg aaattcttcc atgagggtt taccgcgcac ttgatacatg tagatgatgg         600
ttttgccgtt tcgtttgttc gctcggtctc tttgtcccac aaacatatct tgcatgatgt       660
agttgttgtt agtatcgact caaatattta ctctctccaa ccagtaaggt tttgctttta      720
tcctagccac ataaaaatca gaaataaaag tactatttgc taaaaatgaa gtgaaagtat       780
tgaattaacc gaaatcaatg tattcaaatt ttgtctcgct tttctttgt cgactaatat       840
attatcattt gaagataata tataacttt ccaacaaaaa gattatcgac aatttattgt        900
ggtaaatgat tttcaggatg tatccagaat cgacagtcta ccagtactag aatatatcta      960
```

| | |
|---|---|
| atagataaat ggttcttctt acactatgct cattatggat tctttaattt actctttcac | 1020 |
| aaaagggacg atgacgaagg agtctctcta cagcacgtta gaattctttt gataggttta | 1080 |
| cttccattag tctgaaatgg aatcttattt ataagtctgc ctgaaaaatc ttaacaattg | 1140 |
| atattaataa aacggaaaga gtgatgaata tttttaagag catctcgaat ctatctctat | 1200 |
| ttttatttat atactctatt tttgtattta tttaactcta actcatctct attttcattt | 1260 |
| gtaaaataga aatttctaat tttttttttaa agcaaaaaat agagattttt atttttctc | 1320 |
| ttatttattt tttctaacga attttttgagg aaccattaaa gttaaaatat aaatctctat | 1380 |
| tatatttttt cctctatatt cagaaagaaa ataatagaaa caaacattgg agatggttaa | 1440 |
| agcttttttt tttgtccgga taaatatcat acaatatatt tatgtaaata tcaaatttaa | 1500 |
| ataattttct tataactatt ttttaatgcg accttatttc caaagaaagt gttaagccaa | 1560 |
| attaaatcat acatggtaaa taagaggtcc aaaagaccaa aagcattaaa tttaaggtaa | 1620 |
| tgcgtctgat ttcttttctc ccaaacgaaa ggagccaaaa gcaaccgatc aagtggagac | 1680 |
| cagtaaccgc acattcactt catttccccc acaagagaaa agataagata atggagtttt | 1740 |
| ctgccacgtg gccttatcct agtggtgcgt accgataagg gtgtcaacac ctttccttaa | 1800 |
| tcctgtggca gtaaacgacg ttatcatgaa tcatggaccc tttgatcatg agggcttttc | 1860 |
| gcctttaggg ggttctcatt atataaagat gacaacacca gtaggaaaac aagtcagtaa | 1920 |
| gtaaacgagc aaaagaagaa gagaaacaac aagaagtagt aatg | 1964 |

<210> SEQ ID NO 9
<211> LENGTH: 1933
<212> TYPE: DNA
<213> ORGANISM: Arabidopsis thaliana

<400> SEQUENCE: 9

| | |
|---|---|
| aactcttttc ccgataatat tcttcctctc tatccgacac acttccttttt ctccttggag | 60 |
| gtgatgggat ctgcatccaa caagtaagtt gtggtaccaa gattttagtt tacaaactat | 120 |
| cagctttcca ctagacacat tgaacaaccc atttaatata ttatttctag cagaagaaca | 180 |
| ttaacaaatg acccaataag atagcaccag agacagaaca ggggtaaagt tcaaatgact | 240 |
| atagagtggt ggtgaagttc aagacatggt agacctgtgt gcgcgacata tatcttccct | 300 |
| caggcggaag ctgaataccg agcttttttca aatcttcatg agggattggt cgtctgatat | 360 |
| taacaaatag aaagaatgcc catttcatga ccactatgtt tagctggtgt tatctctgga | 420 |
| catgctaaag gaagagtaaa gcaaaaccat acaagggagc acggaatggt ctatctcgtc | 480 |
| ctccaaagcg aagttgtccg gattcttttcc taccaccaag gccacctcct gttaagagag | 540 |
| aaatagattt catctgtaag ggatgaaaat ataacgccta tgacatttca ttacagacaa | 600 |
| aaataaaggt aaagaatggc aaacctagtc ttcttggtat ccatccaggc atcaattgct | 660 |
| gtctattata atcaacaata atctctcgcc catctattag tgaatgatga gcatcctgct | 720 |
| aaagaaacac caaaaaaatt ctcactctga taaacaaact ccactagttt ccagtaatta | 780 |
| cacggagatg ttaatgaaac aatcacattg cggtgcctta gtaagtggtt cagacagctt | 840 |
| tcaacaacaa aaacaagagg taaaagaaa atgcaattta gtatcacagc acctcataag | 900 |
| cacgaagcat ctccttttca gtctcatact ccacaaaacc atatcctcgt gaagctcccg | 960 |
| tcactaaaaa aagtaacaa gaagaggaga ctcaatacta cacaatgtgg aacttagagg | 1020 |
| aaatatgtaa tcacagttct gcttagacaa atatcttggt agaaagtaac aaaccatcag | 1080 |
| aaatagaaag atgataaatt tcctaaagat aaagcaaagt gttgatgtca aagtagagc | 1140 |

```
aattgcaaaa tcttaccaat gtgtcttacc aagcgcaagt tcttaatcct gccatactta    1200
ctcatcacct acgaagaaga aacttttata atcatattca aaacatagtc tacacgaaaa    1260
tcaaaaacta agtgaaattt caatcattaa cctctcgaag tgtatcctcc gtagtgtgat    1320
gagagagacg acccacgaag agagtacagt aaggatctcc aacagccttc gaatcaccag    1380
aaggatcatc tttcaaaaca acccaaatca atgtatttga attcagaaac caaacgataa    1440
aagtgaaaag aggagcagag agaacgagag agtatacata cataagccag cgttataaca    1500
gagaagagct cgacggacgc cgttatcatg tggagcaaca tcagttccgt cgatacttcc    1560
ggcttgaatc ggatgatacg acgtcgcgta gaacactttg ttcacgacgt tgtttcctcc    1620
gccgctcatt tcttctcccc cgactctctc tctctcacgg cggctccggc tgtttaagga    1680
aataaagaat aacgtcgtcg tttgaattga ttactattaa aaagcccaac atataaattg    1740
ggcttattac agcccagtta aagatatatg atattctcgt aggtcccaca cgaaggcgga    1800
aactccaacg gtggctgctt tgggttaggt gaatcactca ctgaagagtg aaaagctcta    1860
gcacaaacca aacaccaaat ctcatttctt cttcttcttc tttttccaca ttttctgatt    1920
agcagatcaa atg                                                       1933
```

ARABIDOPSIS BIO2 GENE PROMOTER

This Application claims the benefit of priority from U.S. Provisional Patent Application No. 60/308,581, filed Jul. 31, 2001.

FIELD AND BACKGROUND OF THE INVENTION

The present invention relates to novel plant promoters and their uses. More particularly, the present invention relates to tissue specific and constitutive plant promoters, expression constructs containing same and plants expressing structural genes or antisense polynucleotides under the control of any of the novel promoters. The invention further relates to methods of identifying minimal functional plant promoter region derived from the novel plant promoters.

The selection of a promoter in the engineering of a heterologous gene expression construct is oftentimes a critical factor in obtaining adequate expression of the desired gene. Promoters are typically found at the 5' upstream regions of coding sequences of genes and are typically directly or indirectly recognized and bound by DNA-dependent RNA polymerases during the initiation of transcription of the coding sequence. Consequently, promoters play a major role in regulating gene expression. There are several general classes of promoters used in the genetic engineering of plants: (i) tissue or organ specific promoters; (ii) developmental stage specific promoters; (iii) inducible promoters; and (iii) constitutive promoters. It will be appreciated that a single promoter may be categorized into more than a single category.

Tissue specific or organ specific promoters drive gene expression in a certain tissue such as in the kernel, root, leaf or tapetum of the plant. Chemical or environmental stimuli such as heat, cold, wounding, infection (e.g., viral, bacterial or fungal infection) and other stress conditions, induce inducible promoters. Although tissue specific and inducible promoters are required for certain applications, constitutive promoters are the most widely used promoters in the transgenic plants industry.

Tissue and developmental stage specific promoters derive the expression of genes, which are expressed in particular tissues or at particular time periods during plant development. Tissue-specific promoters are valuable tools as they permit specific expression of heterologous genes in a tissue and/or developmental stage selective manner, indicating expression of the heterologous gene differentially at a various organs, tissues and/or times, but not in other. Constitutive promoters are defined as those promoters which are capable of driving high levels of gene expression in most or all of the tissues of a plant. Constitutive promoters are useful, for example, for producing herbicide tolerant plants and for many other applications. Presently, the most widely used constitutive promoter in the genetic engineering of plants is the CaMV35S promoter (which is of a viral origin); other widely used constitutive promoters include the maize polyubiquitin promoter and the rice actin promoter.

In general, those familiar with the art agree that constitutive promoters that drive a high level of heterologous gene expression in most of the tissues of a plant are only a few in number and are of considerable value in the field of genetic engineering of crop plants.

It is well recognized among art scholars that there is a widely recognized need for, and it would be highly advantageous to have, novel tissue specific and constitutive plant promoters.

SUMMARY OF THE INVENTION

According to one aspect of the present invention there is provided a method of isolating a minimal functional plant promoter region, the method comprising connecting upstream to a reporter gene a fragment derived from SEQ ID NOs:7, 8 or 9; and testing for a level of expression of the reporter gene in a plant expression system.

According to further features in preferred embodiments of the invention described below, the fragment derived from SEQ ID NOs:7, 8 or 9 is obtained by PCR amplification, restriction with at least one endonuclease or solid phase DNA synthesis.

According to still further features in the described preferred embodiments the plant expression system is a plant cell culture, a transgenic plant or a transiently transformed plant.

According to another aspect of the present invention there is provided a recombinant promoter which is functional in plant cells, wherein the recombinant promoter comprises at least a minimal functional plant promoter region derived from SEQ ID NOs:7, 8 or 9.

According to yet another aspect of the present invention there is provided a n isolated polynucleotide comprising a promoter sequence controlling an expression of a biotin synthase, a ribulose 1,5-bisphosphate carboxylase small subunit, ats3B or a photosystem II type I chlorophyll a/b binding protein of a plant.

According to still another aspect of the present invention there is provided an expression construct comprising the recombinant promoter described herein and a transcription terminator functional in plant cells.

According to further features in preferred embodiments of the invention described below, the expression construct further comprising a structural gene or antisense polynucleotide of interest under control of the recombinant promoter.

According to yet another aspect of the present invention there is provided a plant cell transformed or transfected with a structural gene or an antisense polynucleotide of interest under the control of the recombinant promoter described herein.

According to an additional aspect of the present invention there is provided a plant cell transformed or transfected with the expression construct described herein.

According to yet an additional aspect of the present invention there is provided a method for expressing in plant cells a structural gene or an antisense polynucleotide of interest, the method comprising transforming or transfecting plant cells with the structural gene or an antisense polynucleotide of interest under control of the recombinant promoter described herein.

According to further features in preferred embodiments of the invention described below, the plant cells are part of a whole plant.

According to still further features in the described preferred embodiments the plant cells are isolated from a plant.

According to still an additional aspect of the present invention there is provided a method of constructing an expression construct, the method comprising connecting in an operable 5' to 3' orientation: the recombinant promoter of as described herein; a structural gene or an antisense polynucleotide of interest; and optionally a transcription terminator functional in plant cells.

The present invention successfully addresses the shortcomings of the presently known configurations by providing novel plant promoters which increase the repertoire of plant promoters available for scientific research and commercial applications. In particular, some of the plant promoters described herein perform superior to what is considered the presently most constitutive plant promoter, the CaMV35S promoter. On the other hand, some of the plant promoters described herein are strong tissue specific promoters.

BRIEF DESCRIPTION OF THE DRAWINGS

The file of this patent contains at least one drawing executed in color photograph. Copies of this patent with color photograph(s) will be provided by the Patent and Trademark Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of novel plant promoters, which can be used to derive gene expression in plant cells. Specifically, the present invention is of tissue specific and constitutive plant promoters, expression constructs containing same and plants expressing structural genes or antisense polynucleotides under the control of any of the novel promoters. The invention further relates to methods of identifying minimal functional plant promoter region derived from the novel plant promoters.

The principles and operation of the plant promoters according to the present invention may be better understood with reference to the drawings, examples and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, three novel plant promoters, BIO2 (SEQ ID NO: 9), ats3B (SEQ ID NO: 8) and Lhb1B2 (SEQ ID NO: 7), were isolated from *Arabidopsis thaliana* and their functionality in directing gene expression in plants tested. BIO2 was found to constitutively promote the expression of a gene by 3 and 4 fold higher than the expression obtained by the CaMV35S promoter in shoots and roots, respectively. The ats3B promoter activated gene expression in the shoots mainly, at a 50% higher level than the expression obtained by the CaMV35S promoter. Finally, the Lhb1B2 promoter directed gene expression in the stigma, but not in other plants organs. The gene expression values were two orders of magnitude higher then values obtained for stigmas sampled from CaMV35S positive control plants.

Figure 3A:
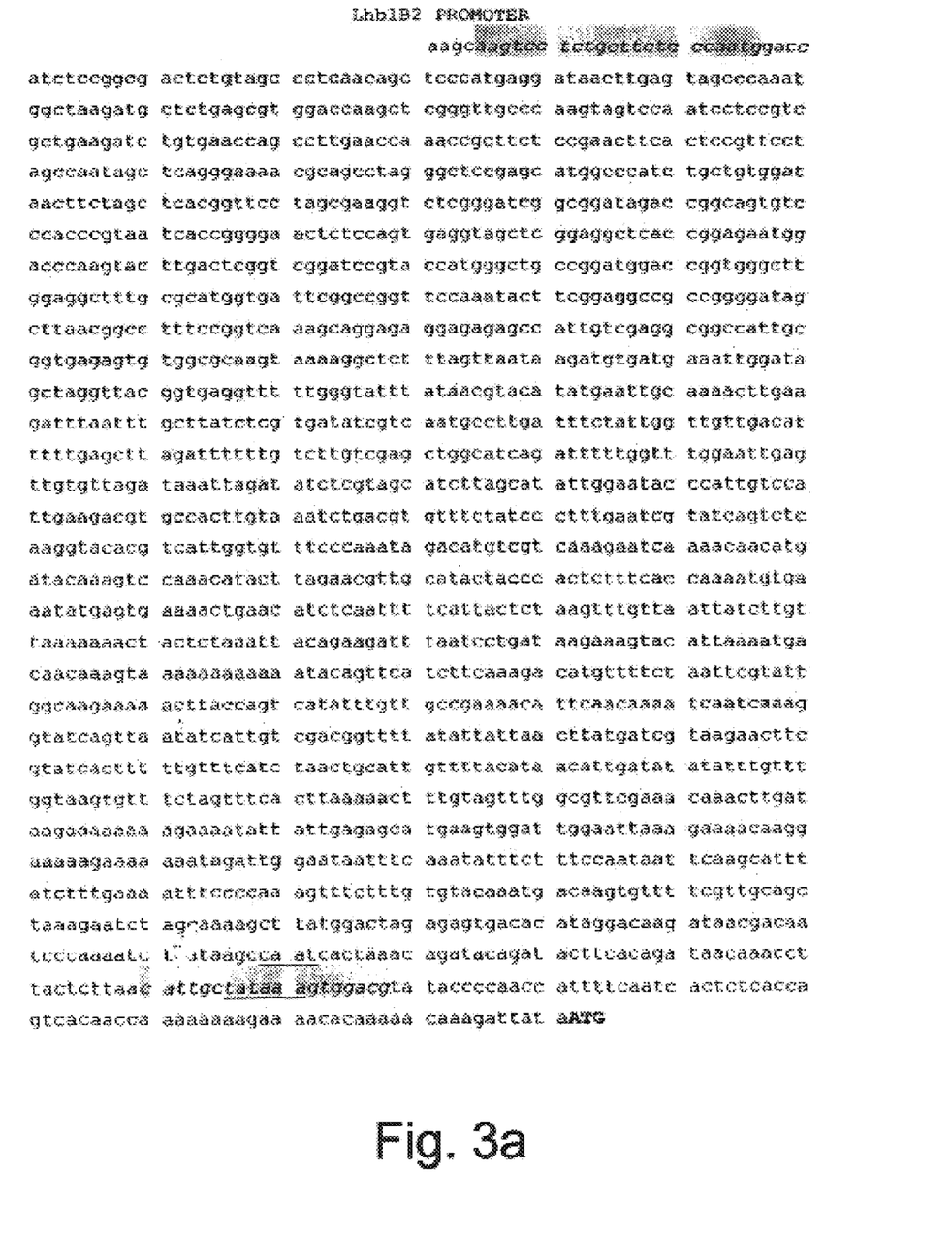
FIGS. 3a–c show exemplary DNA sequences according to the present invention that have plant promoter activity (SEQ ID NOs:7, 8 and 9, respectively). The CAAT and TATA boxes are underlined; the ATG translation start codon is capitalized and bolded and the sequences chosen to design primers to amplify the respective promoter fragments are in Italic font.
Figure 3B:
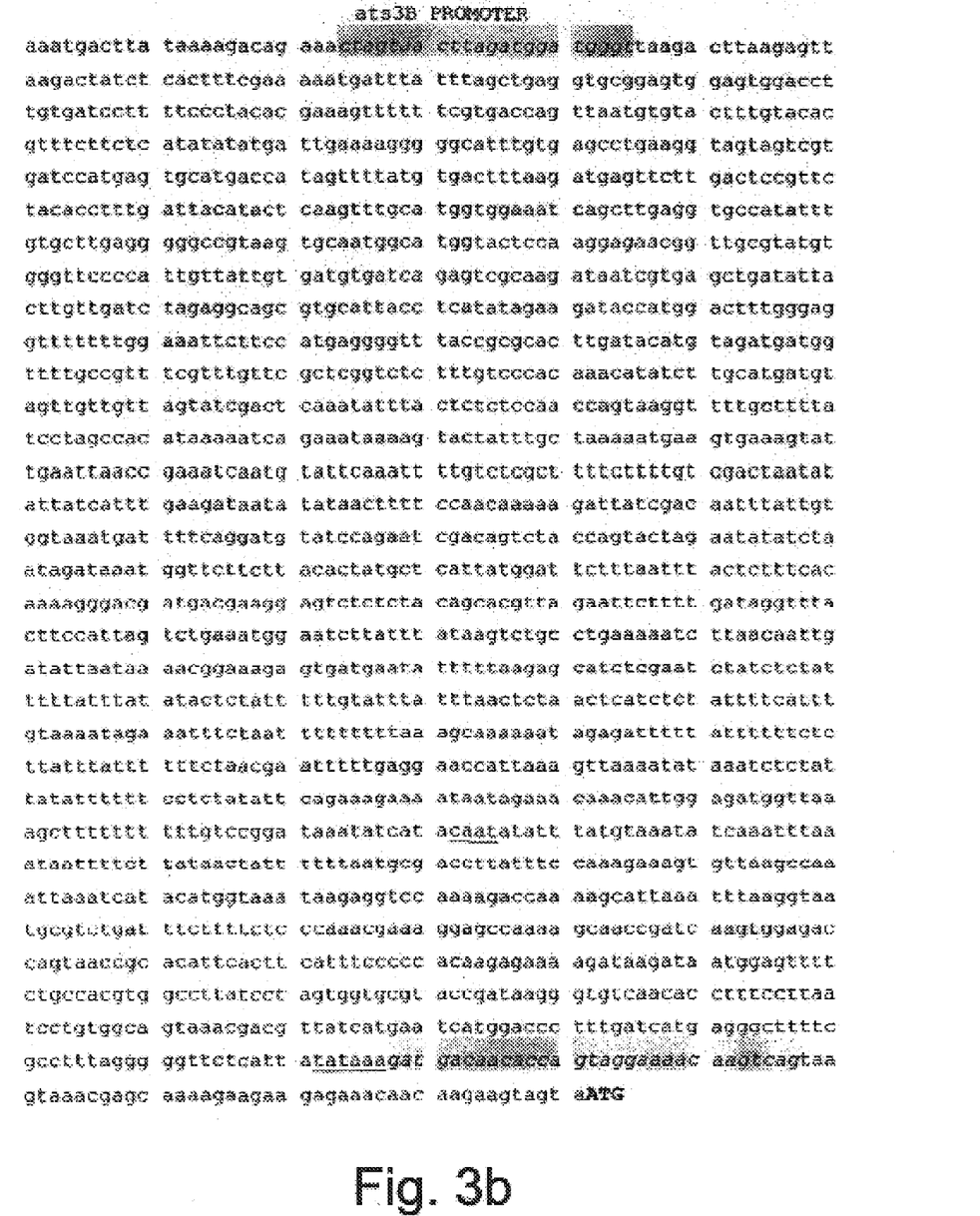
Figure 3C:
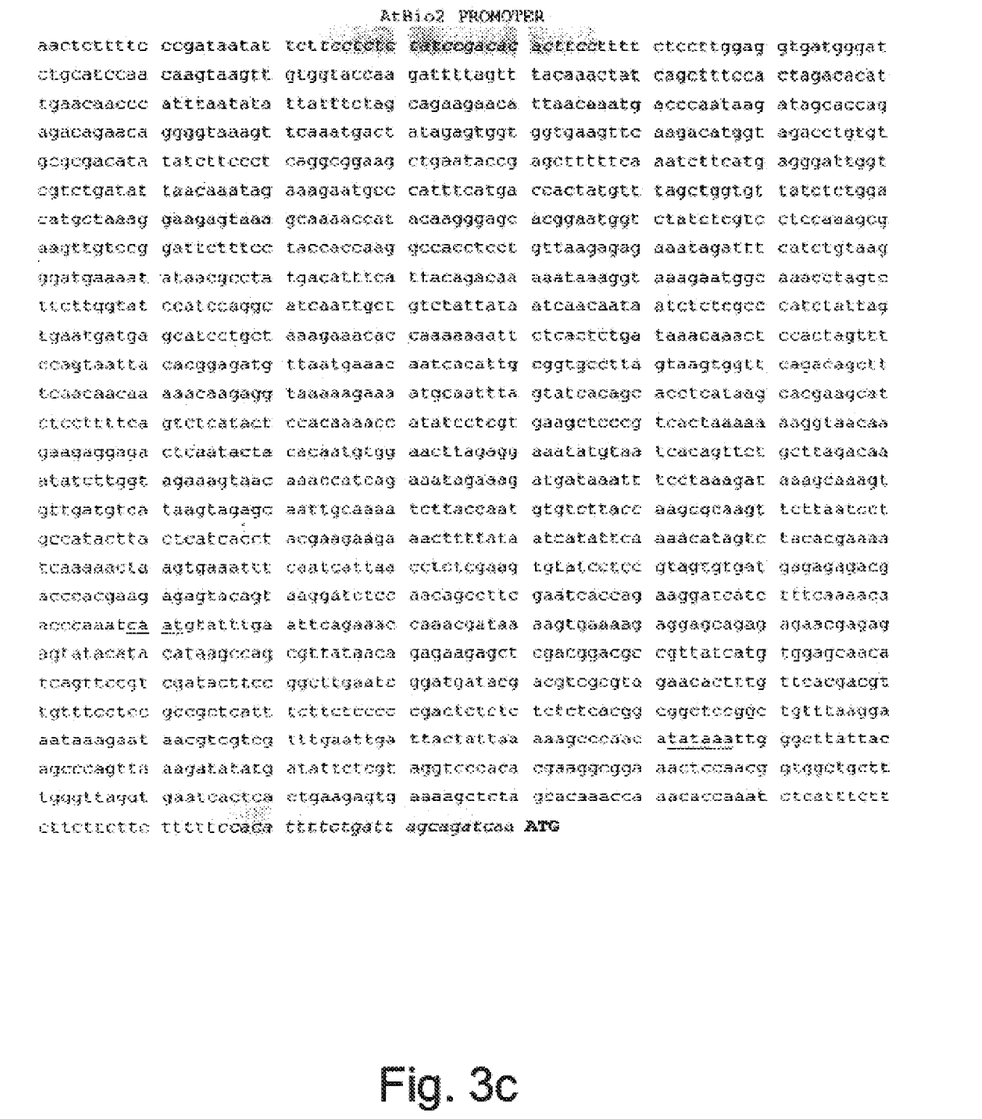

According to one aspect of the present invention there is provided a method of isolating a minimal functional plant promoter region. The method according to this aspect of the invention is effected by connecting by ligation upstream to a reporter gene a fragment derived from SEQ ID NOs:7, 8 or 9; and thereafter testing for a level of expression of the reporter gene in a plant expression system. Several reporter genes such a GUS and various genes encoding fluorescent proteins are highly suitable reporter genes to implement the method described herein. The fragment derived from SEQ ID NOs:7, 8 or 9 can be generated by several methods, including, but not limited to, PCR amplification, restriction with at least one endonuclease or solid phase DNA synthesis. Any plant expression system is suited for the purpose of testing expression of the reporter gene, including, but not limited to, a plant cell culture, a transgenic plant or a transiently transformed plant. Nevertheless, as is evident from the experimental data disclosed herein, while BIO2 constitutively promoted gene expression in shoots and roots, the ats3B promoter activated gene expression mainly in the shoots and the Lhb1B2 promoter directed gene expression in the stigma, but not in other plants organs. Hence, suitable plant cells must be selected for each minimal functional plant promoter region tested. Several promoter/enhancer elements which are further detailed in context of FIGS. 3a–c were uncovered in the promoter sequences isolated. These include a TATA box and a CAAT box. Preferably, these elements will be included in the minimal functional plant promoter region of the invention. It will be appreciated that intervening sequences present between the active element can in many cases be discarded without substantially affecting promoter activity. Hence, the phrase "minimal functional plant promoter region" is used herein to describe both a continuous region derived from SEQ ID NOs:7, 8 or 9 or discontinuous regions derived from SEQ ID NOs:7, 8 or 9 and connected together. In any case, when testing segments derived from SEQ ID NOs:7, 8 or 9, the level of expression of the reporter gene will be compared to the level of expression of the same reporter gene as directed by SEQ ID NOs:7, 8 or 9 themselves, so as to test for lose and/or gain of promoter activity.

According to another aspect of the present invention there is provided a recombinant promoter which is functional in plant cells. The recombinant promoter comprises at least a minimal functional plant promoter region derived from SEQ ID NOs:7, 8 or 9.

According to yet another aspect of the present invention there is provided a n isolated polynucleotide comprising a promoter sequence controlling an expression of a biotin synthase, a ribulose 1,5-bisphosphate carboxylase small subunit, ats3B or a photosystem II type I chlorophyll a/b binding protein of a plant.

According to still another aspect of the present invention there is provided an expression construct. The expression construct comprises the recombinant promoter described herein and a transcription terminator functional in plant cells.

The terminator functional in plant cells to be used in the present invention includes, for example, bacterial-derived terminators such as the terminator from the T-DNA-derived nopaline synthase gene (NOS), or virus-derived terminators usually used in plant genetic engineering techniques, such as the terminators from the Garlic virus GV1 and GV2 genes.

The expression construct of the present invention may comprise a structural gene or an antisense polynucleotide of interest under the control of the recombinant promoter. The structural gene of interest can be any gene whose production by plant cells is desired, including, but not limited to, a gene encoding a therapeutic protein, which therapeutic protein can be hereafter isolated from the plant cells, a gene conferring increase in yield, disease resistance, insect resistance, herbicide tolerance, drought tolerance and/or salt tolerance in plants, or encoding a toxin, which, similar to an antisense polynucleotide can be used to selectively destroy plant tissue when under the control of a tissue specific plant promoter, such as, for example, the Lhb1B2 promoters described herein.

Hence, according to still another aspect of the present invention there is provided a plant cell transformed or transfected with a structural gene or an antisense polynucleotide of interest under the control of the recombinant promoter described herein.

According to an additional aspect of the present invention there is provided a plant cell transformed or transfected with the expression construct described herein.

According to yet an additional aspect of the present invention there is provided a method for expressing in plant cells a structural gene or an antisense polynucleotide of interest, the method comprising transforming or transfecting plant cells with the structural gene or an antisense polynucleotide of interest under control of the recombinant promoter described herein. The plant cells can be a part of a whole plant or the plant cells can be isolated from a plant.

According to still an additional aspect of the present invention there is provided a method of constructing an expression construct, the method comprising connecting in an operable 5' to 3' orientation: the recombinant promoter of as described herein; a structural gene or an antisense polynucleotide of interest; and optionally a transcription terminator functional in plant cells.

The present invention addresses the shortcomings of the prior art by providing novel plant promoters which increase the repertoire of plant promoters available for scientific research and commercial applications. In particular, some of the plant promoters described herein perform superior to what is considered the presently strongest plant promoter, the CaMV35S promoter. Other plant promoters described herein are tissue specific.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Culture of Animal Cells—A Manual of Basic Technique" by Freshney, Wiley-Liss, N.Y. (1994), Third Edition; "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Strains and Plasmids:

*Escherichia coli* strain: XL1-Blue: F':Tn10(Tet$^r$) pro$^+$ lac$^{q?}$ (lacZ)M15/recA1 endA1 gyrA96(Nal$^r$)thi–1hsdR17 (rK$^-$m$_k$$^+$)g1nV44 relA1 lac.

*Agrobacterium tumefaciens* strain: EHA 105.

Vectors:

1. pBluescript II SK.

2. pPME binary vector.

3. pPZP111 binary vector (Hajdukeiwicz et al., 1994).

Figure 1:
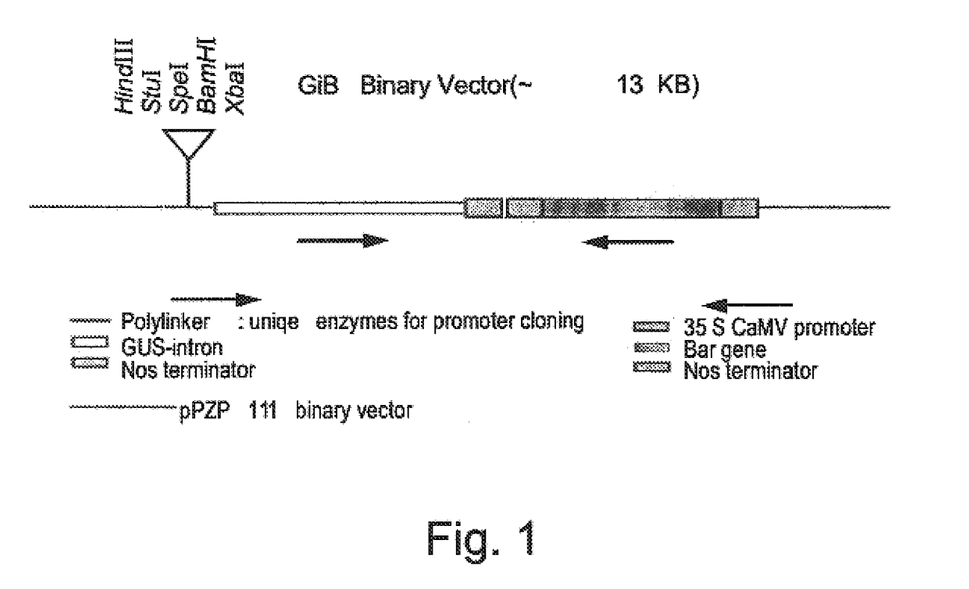
FIG. 1 is a schematic presentation of the pGIB binary vector used while reducing the present invention to practice.

4. pGIB binary vector, constructed as follows: GUS/intron cassette and a Bar gene were excised as a HindIII-EcoRI fragment from pPME vector (Raskind, 1987) and introduced into pPZP binary vector (Hajdukeiwicz et al., 1994). A schematic presentation of this vector is found in FIG. 1.

Plant Cultivars:

Stable and transient expressions were carried out using *Nicotiana tabacum* L. cv. Samson N N. Transient expression analysis was also carried out with *Arabidopsis thaliana* ecotype Columbia.

Promoters Isolation

EST sequences and the corresponding mRNAs were identified within the relevant BAC sequences of *Arabidopsis thaliana* database (Table 1).

TABLE 1

List of the *A. thaliana* genes whose suspected promoters were fused to the Gus gene

| NAME | GENE |
|---|---|
| Actin2* | ACT2 |
| Rubisco activase* | rca |
| Biotin synthase | BIO2 |
| Ribulose 1,5-bisphosphate carboxylase small subunit, ats3B | ats3B |
| Photosystem II type I chlorophyll a/b binding protein | Lhb1B2 |

*Promoter is known in the art and served as positive control.

A sequence of about 1,800–2,000 bp upstream to the ATG translation start site (as was annotated in the database) was amplified using PCR with specific primers designed to contain unique cloning restriction sites.

The PCR products were first cloned into the bluescript pSK vector (Stratagene, blunt ended by SmaI). The suspected promoter fragment was excised and cloned into pGIB vector upstream to the gus reporter gene, using the pre-designed restriction sites.

List of Specific Amplification Primers and Cloning Strategies:

BIO2 Promoter:

A fragment of 1933 bp upstream to the BIO2 coding sequence was isolated, ending 2 nucleotides before the ATG codon.

Primers Used:

```
                                          (SEQ ID NO:1)
5BIO:    5'-GTA
         AGGCCTTCCTCTCTACCGACACACTTCC-3' and (SEQ ID NO:2)
and 3BIO: 5'-GTATCTAGAGATCTGCTAATCAGAAAATGTGG-3'.
```

Underlined letters represent restriction sites for cloning: StuI in 5BIO and XbaI in 3BIO. Bolded letters indicate nucleotides added for the protection of the restriction sites.

ats3B Promoter:

A fragment of 1898 bp upstream to the ats3B coding sequence was isolated, ending 44 nucleotides before the ATG codon.

Primers Used:

```
                                          (SEQ ID NO:3)
5ATS3B:   5'-GTA
          AGGCCTCTAGTAACTTAGATGGATGGGT-3' and (SEQ ID NO:4)
and 3ATS3B: 5'-GTAAGGCCTCTGACTTGTTTTCCTACTGGTGT-3'.
```

Underlined letters represent restriction sites for cloning: both amplification primers contain StuI sequences. Bolded letters indicate nucleotides added for the protection of the restriction sites.

LH1B2 Promoter:

A fragment of 1793 bp upstream to the LH1B2 coding sequence was isolated, ending 73 nucleotides before the ATG codon.

Primers Used:

```
                                          (SEQ ID NO:5)
5B2:      5'-GTAAGGCCTAAGTCCTCTGCTTCTCCCAATG-3'

(SEQ ID NO:6)
and 3B2:  5'-GTATCTAGACGTCCACTTTATAGCAATG-3'.
```

Underlined letters represent restriction sites for cloning: StuI in primer 5B2 and XbaI in primer 3B2. Bolded letters indicate nucleotides added for the protection of the restriction sites.

PCR Amplifications:

Genomic *A. thaliana* DNA (60 ng) was used as template in a 50 µl reaction mixture containing buffer (20 mM KCl, 100 mM TrisHCl pH 7.5), 1 µM of each primer, 200 µM of each dNTP (Pharmacia) and 0.5 units of Pwo DNA Polymerase (Roche). DNA denaturation was performed at 95° C. for 2 minutes, followed by 32 amplification cycles executed at 94° C., 30 seconds, 55–60° C., 45 seconds, 72° C., 45 seconds, and a final extension time at 72° C. of 7 minutes.

Plant Transformations:

I. Transient Expression:

Transient expression assay was done in *A. thaliana* seedlings as follows: A culture of *A. tumefaciens* was grown overnight in LB medium containing rifampicin (50 mg per ml) and kanamicin (25 mg per ml). Bacterial cells (from 3 ml culture) were washed twice with 3 ml of 10 mM $MgSO_4$ and resuspended in 10 ml MS medium to a final $A_{600}$=0.6.

*A. thaliana* seeds were surface sterilized and allowed to germinated for 2 weeks on sterile half strength MS medium plates solidified with agar agar (1%) in a growth chamber at 25° C. with 16 light hours per day.

The bacterial preparation (inoculum) was introduced into 30 seedlings using vacuum infiltration (0.15 atmospheres, 5 minutes) technique. After the infiltration seedlings were blotted dry on sterile Whatman paper and co-cultivated with the bacterial cells for 3 days in a growth chamber (25° C., 16 hours light per day). Following the incubation (co-cultivation) seedlings were washed in sterile 10 mM $MgSO_4$ prior to GUS determination. In most experiments protein was extracted for the GUS assay and results were expressed per unit of protein extracted.

II. Stable Transformation (*A. tumefaciens*-Mediated Transformation of Tobacco):

The stable transformation of tobacco plants was performed according to An et al. (1986) with a few modifications.

Young leaves were taken from a healthy *N. tabacum* plant grown in the greenhouse and surface sterilized. Leaves were cut into 0.5-cm squares and floated upside down on MS104 medium (MS vitamins; Sigma), 30 g $l^{-1}$ sucrose, 1 mg $l^{-1}$6-benzylaminopurine and 100 µg $l^{-1}$1-naphthaleneacetic acid (1-NAA, pH 5.8).

One hundred milliliters of LB (supplemented with 100 µg $ml^{-1}$ kanamycin) were inoculated with 1 ml of a 48 hours culture of *A. tumefaciens* strain carrying the tested plasmid. The culture was incubated at 30° C. until mid-log phase ($A_{600}$=0.5) and aliquots of 50 µl or 500 µl were added to the MS104 medium with the leaf pieces. Following 20 minutes of co-cultivation, the leaf disks were washed in a liquid MS104 and transferred onto MS plates containing 100 µg ml$^{-1}$ kanamycin and 0.8 µg ml$^{-1}$ IAA. After 48 hours of incubation they were re-transferred onto fresh MSII medium (Sigma) plates containing: 0.8% bactoagar, 100 µg ml$^{-1}$ kanamycin, 500 µg ml$^{-1}$ claforan, 0.8 µg ml$^{-1}$ IAA and 2 µg ml$^{-1}$ Kinetin. The leaf pieces were transferred to fresh medium once a week until shoots developed. The largest shoot from each leaf piece was cut away and transferred to MSIII medium (Sigma), 0.8% bactoagar, containing 100 µg ml$^{-1}$ kanamycin 500 µg ml$^{-1}$ claforan. The shoots were transferred to fresh MSIII every 2 weeks until roots developed. Plantlets that were rooted in the media were transferred to a peat-base rooting media and after 3 weeks of hardening in growth chamber were potted in the greenhouse.

Expression Analysis:

Gus activity was analyzed with a fluorimetric MUG assay and a histochemical X-Gluc assay as described previously by Jefferson et al. (1987), with the following modifications:

Fluorimetric Detection of Gus Activity:

125 mg plant tissue was ground in 500 µl of Gus extraction buffer (50 mM Na$_2$HPO$_4$ (pH 7.0), 10 mM β-mercaptoethanol, 10 mM Na$_2$EDTA, 0.1% sodium lauryl sarcosine, 0.1% triton X-100). Cell debris was removed by centrifugation (5 minutes, 4° C., 10,000 r.p.m.) and 300 µl of the supernatant were transferred to a fresh 1.5 ml tube containing 300 µl of extraction buffer with 2 mM 4-methyl umbelliferyl glucoronide (MUG). The mixture was incubated at 37° C. for 30 minutes–1.5 hour followed by removal of 100 µl sample into a tube containing 1,900 µl 0.2 M Na$_2$CO$_3$ to stop the reaction. The progress of the reaction was monitored using a TKO 100 Hoefer Fluorimeter. The sample was excited at 365 nm and the fluorescence, detected at 460 nm. The fluorimeter was calibrated by recording the fluorescence of a series of known 4-MU standards in the range 100–10,000 pmol ml$^{-1}$. The total amount of protein in each reaction was determined based on the technique of Bradford (1976). Specific activities for the enzyme extracts were calculated and expressed in nmoles of 4-MU produced per milligram of protein per minute. Each assay was repeated three times.

Histochemical Detection of Gus Activity

Plant tissue was suspended in Gus assay solution with 1 mg ml$^{-1}$ of X-gluc, briefly vacuum infiltrated and incubated at 37° C. overnight. Chlorophyll was removed by immersion in 100% ethanol overnight.

Experimental Results

Transient Expression Experiments:

Experiments were carried with three replicates for each treatment and values were calculated for each promoter activity as nM product per min for one mg protein. The results which are summarized in Table 2 indicate that all the tested promoter regions induced GUS activity, and that the BIO2 promoter is the strongest one.

TABLE 2

Summary of transient expression assay

| Promoter fragment | Gus activity (nM MU min$^{-1}$ per mg protein) |
|---|---|
| Negative Control | 838 ± 43 |
| GIB (promoterless vector) | 643 ± 33 |
| 35S | 2226 ± 473 |
| rca | 871 ± 110 |
| ACT2 | 1251 ± 206 |
| BIO2 | 2375 ± 394 |

TABLE 2-continued

Summary of transient expression assay

| Promoter fragment | Gus activity (nM MU min$^{-1}$ per mg protein) |
|---|---|
| ats3B | 726 ± 6 |
| Lhb1B2 | 688 ± 64 |

GUS activity was determined in A. thaliana seedlings using the MUG assay. Activity is expressed as nM MU min$^{-1}$ per mg protein with SE of 3 replicates. GIB—vector construct without any promoter, control—MUG assay of plants without transformation.

Stable Transformation

Figure 2A:
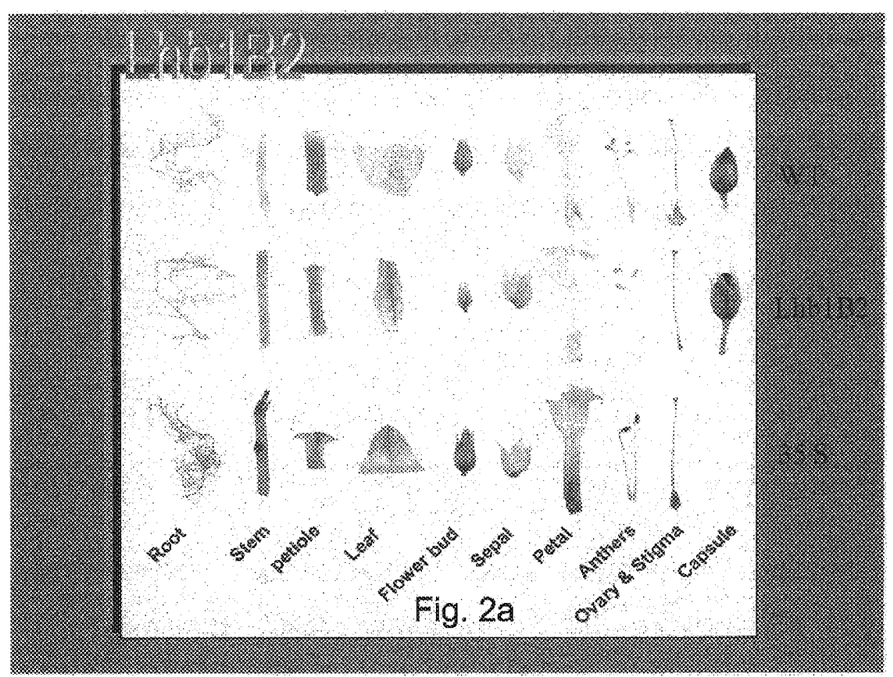
FIGS. 2a–c demonstrate GUS staining of transgenic tobacco plants. Tobacco plants were transformed with the GIB constructs containing promoter sequences fused to uidA or gus reporter gene. 2a—Lhb1B2 promoter; 2b—ats3B promoter; 2c—BIO2 promoter, as compared to wild type (WT) plants and plants expressing the reporter gene under the control of CaMV35S promoter.
Figure 2B:
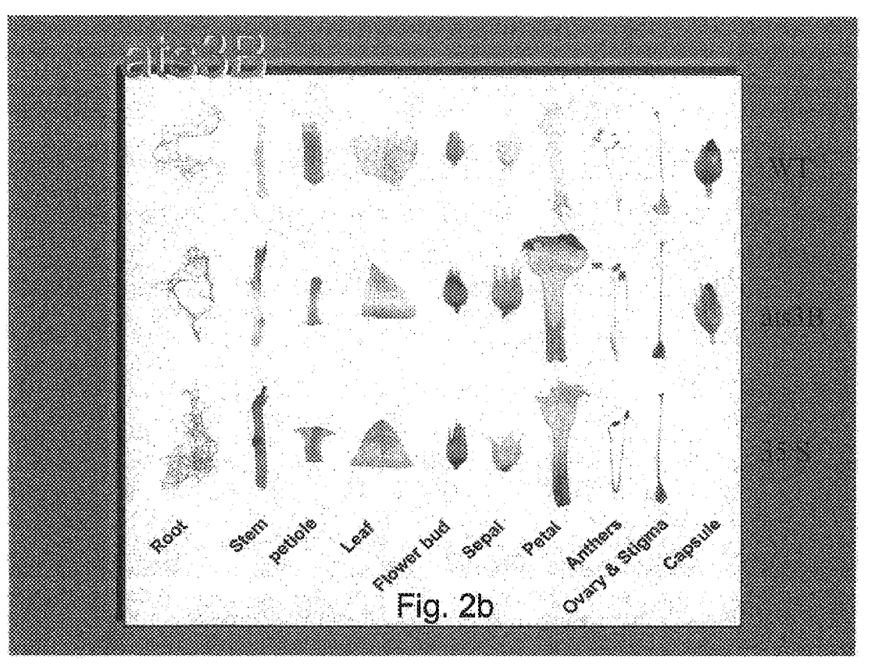
Figure 2C:
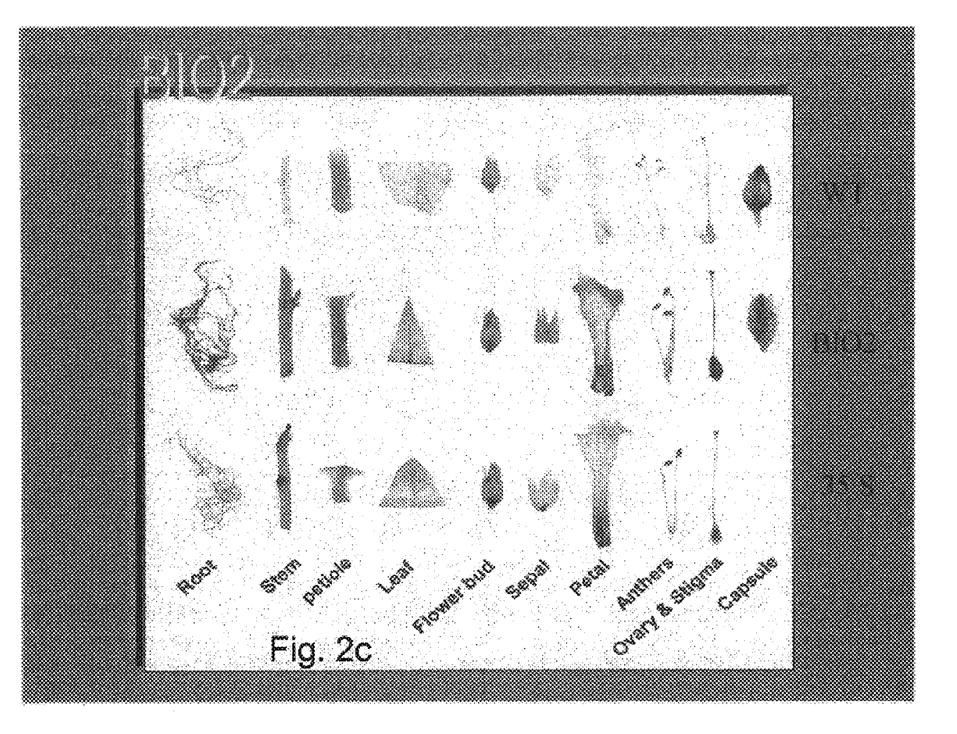

Transgenic plants were identified using the PCR method with Gus-specific primers. Plants were transferred to the greenhouse and allowed to grow in natural lighting schedule. At flowering, plants were sampled for X-gluc staining analysis. Samples of young (emerging) leaves, roots, stems, petioles, flower buds, petals, sepals, pistils and stigmas, anthers and postanthesis-developing ovules from flowering transgenic plants were incubated overnight with GUS staining solution at 37° C. GUS expression was detected in all transgenic plants tested and blue color could not be detected in nontransgenic (control) plants (FIGS. 2a–2c). BIO2 promoter was found to induce staining in all tested plant tissues whereas; Lhb1B2 was active in the stigma and ats3B in the plant shoots but not in the roots.

Quantitative analysis for GUS expression (MUG assay) was carried with all the transformed tobacco plants. Gus activities were detected in young leaves, petioles and roots of transgenic plants (Table 3).

TABLE 3

Summary of stable transformation result

| Promoter fragment | Plant organ examined | Gus activity (nM/min/mg protein) |
|---|---|---|
| rca | leaf | 820 ± 95 |
| | petiole | 1,080 ± 314 |
| | root | 158 ± 6 |
| ACT2 | leaf | 26 ± 5 |
| | petiole | 306 ± 51 |
| | root | 300 ± 133 |
| 35S | leaf | 1,748 ± 310 |
| | petiole | 1,758 ± 159 |
| | root | 3,862 ± 82 |
| BIO2 | leaf | 4,547 ± 238 |
| | petiole | 11,670 ± 923 |
| | root | 12,980 ± 427 |
| ats3B | leaf | 3,408 ± 177 |
| | petiole | 2,725 ± 1,005 |
| | root | 389 ± 47 |
| Lhb1B2 | leaf | 5 ± 2 |
| | petiole | 81 ± 30 |
| | root | 28 ± 13 |

GUS activity was determined in N. tabacum tissues (at flowering stage) using the MUG assay. Activity is expressed as nM MU min$^{-1}$ per mg protein with SE of three replicates.

The Gus activity promoted by BIO2 (biotin synthase promoter) in leaves was three fold higher than that in leaves of the 35S/GUS transgenic plant; in petioles and roots the corresponding increases were five and three fold higher than the respective organs in the 35S/GUS plants. GUS activity in leaves of ats3B (Ribulose 1,5-bisphosphate carboxylase small subunit) plants was 1.4 fold higher than in leaves of the control plants (35S/GUS); however, ats3B petioles and roots showed a significantly lower GUS activity than that of the 35S/GUS petioles and roots, by factors of 1.2 and 14.8, respectively. GUS activity for the Lhb1B2 (Photosystem II type I chlorophyll a/b binding protein) transgenic plants indicated a significant induction in the flower stigma relative to other plant organs of that transgenic plant. These GUS values were two orders of magnitude higher then values obtained for stigmas sampled from the 35S control plants (Table 4).

TABLE 4

Activity of β-glucuronidase in 30 stigmas of transformed tobacco plants with the Lhb1B2 promoter fused to gus gene

| Promoter fragment | Gus activity (nM/min/mg protein) |
|---|---|
| Lhb1B2 | 173.0 |
| 35S | 23.8 |
| WT | 0.0 |

Evaluation was carried out at mid flowering stage in comparison to the activity of β-glucuronidase in stigmas of 35S/gus transformed and non-transformed tobacco plants.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

Bruce W B, Chistenses A H, Klein T, Fromm M and Quail P H (1989) Photoregulation of a phytochrome gene promoter from oat transferred into rice by particle bombardment. Proc Nati Acad, Sci USA 86:9692–9696.

Christensen A H, Sharrock R A, Quail P H (1992) Maize polyubiquitin genes:structure, thermal perturbation of expression and transcript splicing, and promoter activity following transfer to pro Hajdukiewicz, P., Svab, Z. and Maliga, P. (1994) The small versatile pPZP family of Agrobacterium binary vectors for plant transformation. Plant Mol. Biol. 25:989–994.

Hood, E. E., Gelvin, S. B., Melchers, L. S., Hoekema, A. 1993. New Agrobacterium helper plasmids for gene transfer to plants. Transgenic Research 2:208–218.

Jefferson R A (1987) Assaying chimeric genes in plants: the GUS gene fusion system. Plant Mol Biol Reptr 5:387–405.

Lu C A, Lim E K and Yu S M (1998) Sugar response sequence in the promoter of a rice amylase gene serves as a transcriptional enhancer. J Biol Chem 273:10120–10131.

McElroy D, Zhang W. Cao J and Wu R (1990) Isolation of an efficient actin promoter for use in rice transformation. Plant Cell 2:163–171.

Sagi L, Panis B, Remy S, Schoofs H, De Smet K Swennen R and Cammue BPA (1995) Genetic transformation of banana and platain (musa spp.) via paricle bombardment. Bio/Technology 13:481–485.

What is claimed is:

1. A method of identifying a functional plant promoter region, the method comprising:
    (a) connecting a fragment of SEQ ID NO:9 to a reporter gene, said fragment obtained by PCR amplification, restriction with at least one endonuclease or solid phase DNA synthesis;
    (b) testing for an expression of said reporter gene in a plant expression system; and
    (c) identifying a plant expression system exhibiting said expression of said reporter gene, thereby identifying the functional plant promoter region of SEQ ID NO: 9.

2. The method of claim 1, wherein said plant expression system is a plant cell culture, a transgenic plant or a transiently transformed plant.

3. A recombinant promoter which is functional in plant cells, the recombinant promoter comprising the polynucleotide sequence set forth in SEQ ID NO:9.

4. An expression construct comprising the recombinant promoter of claim 3 and a transcription terminator functional in plant cells.

5. The expression construct of claim 4, further comprising a structural gene of interest operably linked to said recombinant promoter.

6. The expression construct of claim 4, further comprising an antisense polynucleotide of interest operably linked to said recombinant promoter.

7. A plant cell transformed or transfected with a structural gene of interest operably linked to the recombinant promoter of claim 3.

8. A plant cell transformed or transfected with an antisense polynucleotide of interest operably linked to the recombinant promoter of claim 3.

9. A plant cell transformed or transfected with the expression construct of claim 5.

10. A method of expressing in plant cells a structural gene of interest, the method comprising transforming or transfecting the plant cells with the expression construct of claim 4, said wherein expression construct includes the structural gene of interest, thereby expressing said structural gene of interest in said plant cells.

11. A method of expressing in plant cells an antisense polynucleotide of interest, the method comprising transforming or transfecting the plant cells with the expression construct of claim 6.

12. The method of claim 10, wherein said plant cells are part of a whole plant.

13. The method of claim 10, wherein said plant cells are isolated from a plant.

14. A method of constructing an expression construct, the method comprising connecting in an operable 5' to 3' orientation:
    (a) the polynucleotide sequence set forth in SEQ ID NO:9;
    (b) a structural gene of interest operably linked to said polynucleotide; and
    (c) a transcription terminator functional in plant cells.

15. A method of constructing an expression construct, the method comprising connecting in an operable 5' to 3' orientation:
    (a) the polynucleotide sequence set forth in SEQ ID NO:9;
    (b) an antisense polynucleotide of interest operably linked to said polynucleotide; and
    (c) a transcription terminator functional in plant cells.

16. An isolated polynucleotide comprising a promoter sequence consisting of the polynucleotide sequence set forth in SEQ ID NO: 9, controlling transcription of a biotin synthase gene of a plant.

17. The method of claim 11, wherein said plant cells are part of a whole plant.

18. The method of claim 11, wherein said plant cells are isolated from a plant.

* * * * *